United States Patent [19]
Kierzkowski et al.

[11] Patent Number: 6,069,113
[45] Date of Patent: May 30, 2000

[54] FORMULATED COPPER ALGAECIDES

[75] Inventors: David J. Kierzkowski, Cumming; John D. Puetz, Duluth; Gang Wei, Doraville, all of Ga.

[73] Assignee: Laporte Water Technologies & Biochem, Inc., Alpharetta, Ga.

[21] Appl. No.: 09/152,182

[22] Filed: Sep. 14, 1998

Related U.S. Application Data

[60] Provisional application No. 60/059,757, Sep. 23, 1997.
[51] Int. Cl.[7] ............................. A01N 25/32; A01N 59/20
[52] U.S. Cl. ............................................. 504/152
[58] Field of Search ................................. 504/152

[56] References Cited

U.S. PATENT DOCUMENTS

| | | | |
|---|---|---|---|
| 4,324,578 | 4/1982 | Seymour et al. | 71/67 |
| 4,361,435 | 11/1982 | Meyers et al. | 71/66 |
| 4,418,648 | 12/1983 | Lightner | 119/2 |
| 4,505,734 | 3/1985 | Freedenthal et al. | 71/67 |
| 4,518,506 | 5/1985 | Green et al. | 210/747 |
| 4,983,389 | 1/1991 | Levy | 424/406 |
| 4,983,390 | 1/1991 | Levy | 424/404 |
| 4,985,251 | 1/1991 | Levy | 424/404 |
| 5,407,899 | 4/1995 | Howell | 504/152 |

*Primary Examiner*—S. Mark Clardy
*Attorney, Agent, or Firm*—McAndrews, Held & Malloy, Ltd.

[57] ABSTRACT

A composition comprising a terpene, an emulsifier, and a copper complex is provided, along with methods for its use as an algaecide. The composition is effective when used as an algaecide to treat algae growth in aquatic environments, even though it contains much less terpene than other commonly-used algaecides and can be used without a conventional surfactant. The composition is also less toxic and less flammable than other commonly-used algaecides.

19 Claims, No Drawings

FORMULATED COPPER ALGAECIDES

CROSS-REFERENCE TO RELATED APPLICATIONS

A corresponding provisional application was filed on Sep. 23, 1997 as U.S. Ser. No. 60/059,757. The priority of that provisional application is claimed here.

STATEMENT REGARDING FEDERALLY SPONSORED RESEARCH OR DEVELOPMENT

Not applicable.

BACKGROUND OF THE INVENTION

The present invention relates to a composition active as an algaecide and a herbicide. In particular, the present invention relates to a composition for use in aquatic environments to control algae and aquatic plants. As used herein, the terms "algaecide" and "algaecidal" are meant to be used interchangeably and/or in conjunction with the terms "herbicide" and "herbicidal". Similarly, the term "algae" is meant to be used interchangeably and/or in conjunction with the term "aquatic plants".

Various aquatic environments, such as ponds, lakes, rivers, and canals, are susceptible to excessive algae growth. Such growth is undesirable for a number of reasons. For example, the presence of algae can restrict the flow of water and circulation throughout a body of water, resulting in stagnation. Excessive algae can discourage boating, swimming, or other recreational use. Certain strains of algae can cause the build up toxic agents in lakes or rivers, rendering those bodies of water unfit for use as irrigation sources. And for ornamental bodies of water, such as fountains and fish ponds, the presence of algae is often simply unsightly.

Copper ions have long been used to control the growth of algae in aquatic environments. In early applications, copper ions were provided by dissolving copper sulfate in the target body of water. Although somewhat effective, copper sulfate is not chemically stable in water. The disassociated copper ions react with carbonates present in the water to produce an insoluble precipitate of copper carbonate. Not only are the precipitated copper ions no longer available to control the algae growth, but the precipitated carbonate which settles at the bottom of the treated body of water may be unduly toxic to desirable plants or animals.

More recently, chelated copper ions in complexed form have been used to treat algae growth. U.S. Pat. No. 4,324,578, which is incorporated herein by reference in its entirety, discloses a method of preparing such a copper complex. The described complex, which consists of copper ions chelated with monoethanolamine and triethanolamine, is useful in that it maintains the copper ions in solution even in the presence of carbonates, unlike copper sulfate. In addition, copper complexes such as those described in U.S. Pat. No. 4,324,578 have improved stability to both heat and light. Despite these advantages, however, complexed copper ions are easily diluted (or carried away by water flow) when applied directly to a body of water. As expected, dilution results in a loss of effectiveness because of decreased contact between the copper ions and the target algae.

To overcome this problem, copper complexes have been combined with a water-insoluble phase, using emulsifiers and wetting agents, to create an emulsion containing copper coordination complexes. Such emulsions enhance the uptake of copper ions from the aqueous solutions by the target algae or other plants. The enhancement is observed in terms of speed of the take-up and quantity of copper ions which penetrate into the physiological system of the organism. One such composition is described in U.S. Pat. No. 5,407,899, which is incorporated herein by reference in its entirety. U.S. Pat. No. 5,407,899 discloses an emulsion consisting of 42.5% by weight of a chelated copper complex, 12.7% by weight of an emulsifier (composed of 8.5% by weight of tall oil fatty acid and 2.7% by weight of triethanolamine), 42.5% by weight of d,1-limonene (a wetting agent and the principle ingredient of the water-insoluble phase), and 3.8% by weight of sodium xylene sulfonate (a surfactant). The emulsion described in U.S. Pat. No. 5,407,899 is commercially available as a product called CLEARIGATE®. Increased copper ion uptake has also been achieved by mixing commercially-available chelated copper complexes with separately-available emulsifier/wetting agent carrier compositions. For example, the well-known copper complex CUTRINE-PLUS® is often used in combination with CIDEKICK®, a carrier composition that contains emulsifying agents and a large proportion of limonene.

There are a number of problems with these existing algaecidal formulations. To begin with, such formulations are flammable and tend to exhibit some toxicity to humans. The flammability is attributable to the presence of large amounts of terpene wetting agents such as limonene. Terpene wetting agents are characteristically highly flammable, and, as would be expected, algaecidal formulations containing large amounts of these agents are therefore also flammable. Increased terpene concentration also contributes to the toxicity of algaecidal formulations. For example, the presence of large amounts of limonene appears to contribute to the dermal toxicity of the algaecide described in U.S. Pat. No. 5,407,899 (which exhibits Category II dermal toxicity under 40 C. F. R. § 156).

The use of large amounts of terpene wetting agents in an algaecide is also expensive. Typical wetting agents such as limonene do not serve as active algaecidal ingredients and, therefore, the presence of large amounts of a wetting agent in a composition tends to displace the active algaecide (for example, the copper complex). As a result, the user must apply greater amounts of the composition to a body of water in order to obtain the desired level of copper to reduce algae growth. Not only is such use of an excess of wetting agent inefficient, it increases the cost of the algaecide.

Another disadvantage to existing algaecidal formulations is that they often contain conventional surfactants. As used herein, the phrase "conventional surfactant" refers generally to any known anionic, nonionic, or amphoteric surfactants such as sulfonates or ethoxylates, but excludes the terpene wetting agents and emulsifiers described herein, to the extent that such compounds may fall under a broad definition of the term "surfactant". The use of a conventional surfactant increases the cost of an algaecide twofold. First, the surfactants themselves tend to be quite expensive—even when added in small quantities. Second, the addition of a surfactant necessitates an additional processing step in the manufacture of the algaecide. Aside from cost issues, surfactants are problematic because they are toxic to certain species of fish. Due to this toxicity, algaecides containing conventional surfactants are unsuitable for use in certain aquatic environments.

An additional problem exists with algaecidal formulations that are prepared by mixing commercially available copper complexes with emulsifier/wetting agent carrier packages: the additional mixing step is costly and inconvenient for the consumer. This is the case with the CUTRINE-PLUS®/

CIDEKICK® mixture referred to above. Because these two products are immiscible, they must be manually agitated both prior to and during application to the target body of water. In practice, one person operates a spraying device to apply the algaecide, while another person continuously agitates the CUTRINE-PLUS®/CIDEKICK® mixture that is being applied. Thus, successful application of this mixture requires either the use of an additional piece of equipment (i.e., an automatic mixing device), or an additional person's time.

BRIEF SUMMARY OF THE INVENTION

Accordingly, an object of the present invention is to provide a formulated copper algaecide that is at least as effective as at least some other copper algaecides and yet uses much less terpene.

Another object of the present invention is to provide a formulated copper algaecide that is less flammable than at least some other algaecides.

An additional object of the invention is to provide a formulated copper algaecide that is less toxic to humans than at least some other algaecides.

Still another object of the invention is to provide a formulated copper algaecide that is more effective than at least some other algaecides.

A still further object of the invention is to provide a formulated copper algaecide that is less costly to manufacture than at least some other copper algaecides.

Yet another object of the invention is to provide a formulated copper algaecide that contains less or none of a conventional surfactant.

Even another object of the invention is to provide a formulated copper algaecide that is less toxic to fish than at least some other algaecides.

Still yet another object of the invention is to provide a formulated copper algaecide that exists as a more stable emulsion than at least some other algaecides.

Other objects of the invention will become apparent to one skilled in the art who has the benefit of the specification and the prior art.

One aspect of the invention which satisfies one or more of the foregoing objects, in whole or in part, is a composition including a copper complex, an emulsifier made from the reaction of a tall oil fatty acid and an alcohol amine, and a terpene in an amount that makes up less than about 5 percent by weight of the composition.

Another aspect of the invention is a composition as previously defined, where the copper complex is made from the reaction of copper carbonate and a chelating agent in an aqueous environment, such as water.

Another aspect of the invention is a composition as previously defined that exists as a stable emulsion.

Still another aspect of the invention is a composition as previously defined that is at least substantially free of a conventional surfactant.

Yet another aspect of the invention is a method of controlling algae in a body of water by spraying a composition as previously defined onto the surface of the water, or by simply adding the composition to the water.

DETAILED DESCRIPTION OF THE INVENTION

The present invention includes a copper complex, a terpene, and an emulsifier formed from tall oil fatty acids and alcohol amines.

Copper complexes contemplated for use in the present invention include any copper-containing compositions wherein copper ions are bioavailable when the composition is present in treated water. One such composition is basic copper sulfate. More preferable are those complexes containing chelated copper ions. Such complexes comprise copper ions bonded to a chelating agent in any manner presently known or developed in the future. One known reaction method is the admixture of copper carbonate and a chelating agent, preferably in an aqueous medium. Chelating agents contemplated for use herein include: sodium tripolyphosphate, hexametaphosphoric acid, ethylenediaminetetraacetic acid, nitrilotriacetic acid, N-dihydroxyethylglycine, ethylenebis(hydroxyphenylglycine), acetylacetone, trifluoro-acetyl-acetone, thenoyltrifluoroacetone, tartaric acid, citric acid, gluconic acid, 5-sulfosalicylic acid, ethylenediamine, diethylenetriamine, triethylenetetramine, triaminotriethylamine, monoethanolamine, triethanolamine, N-hydroxyethyl-ethylenediamine, dipyridil, o-phenanthroline, salicylaldehyde, disulfo-pyrocatechol, chromo-tropic acid, oxine-8-hydroxyquinoline, oxinesulfonic acid, dimethylglyoxime, salicyl-aldoxime, disalicylaldehyde 1,2-propylenediimine, tetraphenyl-porphin, phthalo-cyanine, toluene-dithiol (Dithiol), dimercaptopropanol, thioglycolic acid, potassium ethyl xanthate, sodium diethyldithio-carbamate, dithizone, diethyl dithio-phosphoric acid, thiourea, dibenzo-[18]-crown-6, hexamethyl-[14]-4,11 -dieneN$_4$, (2.2.2-cryptate), polyethyleneimines, polymethacryloylacetone, poly(p-vinylbenzyl-iminodiacetic acid), nitrilotrimethylenephosphonic acid, ethylene-diaminetetra(methylenephosphonic acid), and hydroxy-ethylidenediphosphonic acid. Any other compound falling within the class of compounds known as chelating agents is contemplated for forming a copper complex for use in the inventive composition.

The copper complex can range in elemental copper concentration from between about 1 and about 12 percent or more, alternatively 9 to 10 percent. One commercially available copper source is CUTRINE-PLUS®. CUTRINE-PLUS® is a mixed copper mono and triethanolamine complex and has an elemental copper level of 9.0 percent copper. CUTRINE-PLUS® is available commercially from Laporte Water Technologies & Biochem, Inc., Alpharetta, Ga. 30004. Another suitable copper complex can be formed by mixing 32.4 percent by weight water, 18.3 percent by weight copper carbonate, 22.2 percent by weight monoethanolamine, and 27.1 percent by weight triethanolamine. The other copper complexes identified in the patents incorporated by reference are also contemplated for use in the present invention.

In the present invention, the copper complex is in the inventive composition at between about 10 and about 99 percent by weight. Alternately, the copper complex is in the formula at between 50 and about 99 percent by weight, or between 70 and about 99 percent by weight. Optionally, the copper complex is in the formula at about 94 percent by weight. If the copper complex used is the reaction product of copper carbonate and a chelating agent in an aqueous environment, these constituents may be in the formula as follows: from about 1 to about 84 percent by weight of water, from about 1 to about 87 percent by weight of a chelating agent, and from about 1 to about 27 percent by weight copper carbonate. Alternately, the constituents may be in the formula at from about 3 to about 50 percent by weight of water, from about 5 to about 60 percent by weight of a chelating agent, and from about 2 to about 22 percent by weight copper carbonate.

While the composition is stated above in concentrated form, the inventors contemplated that any volume of water or other diluents can be added to the composition, or vice versa, within the scope of the invention. In that instance, the percentages by weight stated herein can be interpreted as parts by weight, not necessarily totaling 100% by weight.

Another component of the inventive composition is a terpene. A terpene acts as a wetting agent, working in conjunction with an emulsifier to enhance penetration of the plant tissues by the copper ions. Used in this capacity, a terpene improves the absorption rcopper ions copper ions in the inventive composition before the composition is either diluted to ineffective concentrations or separated from the target plants by water flow.

In general, a terpene can be characterized as an unsaturated hydrocarbon based on an isoprene unit, $C_5H_8$. However, any compound falling within the class of compounds known as terpenes or terpene derivatives (often called terpenoids) is contemplated to be suitable for use in the inventive composition. Terpenes (and derivatives) contemplated for use herein include: tricyclene; α-pinene; α-fenchene; camphene; βpinene; myrcene; cis-pinane; cis/trans-p-8-menthene; trans-2-p-menthene; p-3-menthene; trans-p-menthane; 3-carene; cis-p-menthene; 1,4-cineole; 1,8-cineole; αterpinene; p-1-menthene; p-4(8)-menthene; limonene; p-cymene; 7-terpinene; p-3,8-menthadiene; p-2,4(8)-menthadiene; terpinolene; isobornyl methyl ether; α-terpinyl methyl ether; ocimene; α-farnesene; squalene; lycopene; sylvestrenc; zingiberene; γ-carotene; sabinene; camphene; β-selinene; caryophyllene; vetivazulene; β-carotene; cedrene; fenchone; linalool; α-fenchol; citronellal; terpinen-1-ol; camphor; trans-β-terpineol; trans-menthone; terpinene-4-ol; neomenthol; borneol; isoborneol; menthol; y-terpineol; αterpineol; citronellol; nerol; geranial; neral; geraniol; carvone; hydroxycitronellal; 1,8-terpin; α-ionone; β-ionone; and nerolidol.

In contrast to the prior art, which used much more d-limonene or other teipenes, d-limonene can be added to the present formula at levels between about 0.1 and less than about 5.0 percent by weight. Alternately, d-limonene can be added to the present formula at levels of less than about 5.0 percent by weight, wherein the terpene is present at least in an amount effective to function as a wetting agent. As yet other alternatives, d-limonene can be added to the present formula at levels between about 0.1 and about 3 percent by weight, or at levels between about 0.3 and about 2 percent by weight. Optionally, d-limonene can be added at a level of about 1 percent by weight or at a level of about 0.5 percent by weight. The phrase "less than about 5%" as used herein refers to the presence of a terpene at levels greater than 4 percent by weight but less than an amount deemed by one skilled in the art to be about 5 percent by weight as that limitation is used in U.S. Pat. No. 5,407,899. In laboratory formulations, d-limonene was used. However, as described, any form of d-limonene and/or other terpenes are acceptable.

The emulsifier system utilized in the product is a mixture of a tall oil fatty acid and an alcohol amine. Tall oil fatty acids can be characterized as fatty acids which contain less than about 10 percent conjugated unsaturation and having chain lengths of not less than 12 carbon atoms, usually between 16 and 30, but any compound falling within the class of compounds known in the art as tall oil fatty acids may be suitable for use in the inventive composition. One commercially available tall oil fatty acid is SYLFAT FA-2®, a tall oil fatty acid having a chain length of 22 carbon atoms. SYLFAT FA-2® is available commercially from Arizona Chemical, Panama City, Fla. The tall oil fatty acid is admixed with any alcohol amine known in the art to form the emulsifier system used in the present invention. Alcohol amines contemplated for use herein include monoethanolamine, triethanolamine, and N-hydroxyethylethylene-diamine.

The emulsifier blend can have a ratio of tall oil fatty acid to alcohol amine of up to about 2.33:1 by weight. Excess alcohol amine can be added to the formula without any adverse effects on stability, but an increase in tall oil fatty acid has been found to cause separation in certain formulations. The emulsifier blend is added to the inventive formulation at about 1 to about 20 percent by weight. Alternately, the emulsifier blend is added to the formulation at about 1 to about 10 percent by weight, or at about 3 to about 6 percent by weight. Optionally, the emulsifier is added to the formulation at about 5 percent by weight, or at about 5.5 percent by weight. The constituents of the emulsifier blend can be added to the formulation (in lieu of the blend) as follows: from about 0.1 to about 14 percent by weight tall oil fatty acid, and from about 0.3 to about 19 percent by weight of an alcohol amine. Alternately, the constituents can be added at from about 0.5 to about 11 percent by weight tall oil fatty acid, and from about 0.4 to about 10 percent by weight of an alcohol amine. If an alcohol amine is used in the inventive composition as both part of the emulsifier blend and as a chelating agent for the copper complex, such alcohol amine may be added to the present invention in combined form at about 2 to about 90 percent by weight, or alternatively at about 5 to about 70 percent by weight.

While the inventive composition has been generally described as including a copper complex, a terpene, and an emulsifier, any additional ingredients may be used in any amount that does not make the composition ineffective or too dangerous to use. For example, the addition of certain dyes or fragrances would be acceptable. Also, other algaecides or herbicides could be used to complement the copper complex in the inventive composition, without adverse impact on effectiveness or unacceptable toxicity. As mentioned before, any amount of water or other diluents can be added.

The composition of the present invention exists as a stable emulsion, and has algaecidal activity when added to standing water in an amount effective to provide a copper concentration of about 1 ppm or less. The proportion of the composition required to provide a desired level of algaecidal activity, and the proportion of the composition required to provide a desirably low toxicity, can readily be determined by straightforward testing of the composition. The composition can be applied to the target body of water through any method known in the art. One method contemplated for use herein is spraying onto the surface of the target body of water an algaecidally effective amount of the inventive composition.

The formulation of this invention has added advantages over other copper algaecides. Surprisingly, the present invention uses much less terpene and can be used without a conventional surfactant, and yet is more effective than the algaecides identified in the patents previously incorporated by reference. Notably, the formulation is much less flammable than other products or mixtures containing large amounts of terpene.

The inventive composition also exhibits less toxicity to humans than formulated copper products like CLEARIGATE ® and, unexpectedly, stand-alone copper complex formulations such as CUTRINE-PLUS®. Under the classification system of 40 C. F. R. § 156, CLEARIGATE® exhibits Category II inhalation toxicity, Category II dermal toxicity, and Category I eye local effect (with Category I being the most toxic and Category IV being the least). Similarly, CUTRINE-PLUS® exhibits Category II inhalation toxicity, Category III dermal toxicity, Category I skin local effect, and Category I eye local effect. In contrast, the formulation of the present invention (as described in example 1 below) exhibits Category III inhalation toxicity, Category III dermal toxicity, Category III skin local effect, and Category III eye local effect.

Because the formulation reduces or eliminates certain components contained in other copper algaecides, it is less expensive to manufacture. A user of the present formulation also avoids the problems inherent in the use of combined products such as CUTRINE-PLUS® and CIDEKICK® because the inventive composition exists as a stable emulsion. The present invention is particularly effective in ponds and other standing water, where some formulated products are either ineffective or too toxic when used in an effective amount.

EXAMPLE 1

In a 2000-ml flask, add 304.5 grams of water, followed by 208.3 grams of monoethanolamine. Place the flask under a laboratory mixer and put heat-insulating material around the flask. Mix the solution for about 15 minutes. Next, add 172.2 grams of copper carbonate and mix the solution for about 90 minutes. Next, add 255 grams of triethanolamine and mix the solution for about 90 minutes. Remove the heat-insulating material around the flask and let the solution cool down to about room temperature. To the cooled solution add 25 grams of monoethanolamine, followed by 30 grams of tall oil fatty acid and 5 grams of d-limonene. Mix the solution for about 15 minutes. What is produced as a final product is a free flowing blue liquid with the characteristic citrus odor from the d-limonene.

EXAMPLE 2

In a 1000-ml beaker, 940 grams of CUTRINE-PLUS®, a copper complex containing 9% elemental copper from mixed copper-ethanolamine complexes, were added. To that 15 grams of triethanolamine were added. The beaker was placed under a laboratory mixer and the solution was mixed for about one minute. Next, 35 grams of tall oil fatty acid were added. The solution was again mixed until the solution appeared homogeneous, about 2 minutes. Finally, 10 grams of d-limonene were added, and the solution was mixed for about 2 minutes. What was produced as a final product was a free flowing blue liquid with the characteristic citrus odor from the d-limonene.

|  | Present Invention Example 1 | Present Invention Example 2 | U.S. Pat. No. 5,407,899 | Present Invention Broad Range |
| --- | --- | --- | --- | --- |
| d-limonene | 0.5 wt. % | 1.0 wt. % | 42.5 wt. % | (0.1–less than about 5 wt. %) |
| tall oil fatty acid | 3.0 wt. % | 3.5 wt. % | 8.5 wt. % | (1–20 wt. %) |
| alcohol amine | 2.5 wt. % | 1.5 wt. % | 2.7 wt. % | — |
| surfactant (Na xylene sulfonate) | — | — | 3.8 wt. % | — |

-continued

|  | Present Invention Example 1 | Present Invention Example 2 | U.S. Pat. No. 5,407,899 | Present Invention Broad Range |
| --- | --- | --- | --- | --- |
| copper complex | 94.0 wt. % | 94.0 wt. % | 42.5 wt. % | (10–99 wt. %) |
| Total | 100.0 | 100.0. | 100.0 |  |

Algaecidal Effectiveness

A portion of a pond of approximately 5.5 acres in area and having an average depth of 3 feet and having a heavy infestation of Hydrodictyon strain of algae, was treated with the copper algaecide prepared in accordance with Example 1 at a rate of approximately 0.75 gal./acre-foot to provide a copper concentration of approximately 0.25 ppm. After a period of three days more than 95% of the algae had disappeared from the water surface.

A portion of a pond of approximately 2 acres in area and having an average depth of 4 feet and having a heavy infestation of algae, including some resistant Cladophora strain of algae, was treated with the copper algaecide prepared in accordance with Example 1 at a rate of approximately 0.6 gal./acre-foot. After a period of eleven days 99% of the algae had disappeared from the water surface.

What is claimed is:

1. A composition comprising from about 0.1 to less than about 5% by weight of a terpene, from about 1 to about 20% by weight of an emulsifier comprising the reaction product of tall oil fatty acid and an alcohol amine, and from about 10 to about 99% by weight of a copper complex.

2. The composition of claim 1, wherein:

said terpene is present as from about 0.1 to about 3% by weight of the composition;

said emulsifier is present as from about 1 to about 10% by weight of the composition; and said copper complex is present as from about 50 to about 99% by weight of the composition.

3. The composition of claim 1, wherein:

said terpene is present as from about 0.3 to about 2% by weight of the composition;

said emulsifier is present as from about 3 to about 6% by weight of the composition; and said copper complex is present as from about 70 to about 99% by weight of the composition.

4. The composition of claim 1, wherein said composition is a stable emulsion.

5. The composition of claim 1, wherein said composition is at least substantially free of a conventional surfactant.

6. The composition of claim 1, wherein said terpene is limonene.

7. The composition of claim 1, wherein said emulsifier comprises from about 0.5 to about 11% by weight of the complete composition of a tall oil fatty acid, and from about 0.4 to about 10% by weight of the complete composition of an alcohol amine.

8. The composition of claim 1, wherein said alcohol amine is selected from the group consisting of monoethanolamine and triethanolamine.

9. The composition of claim 1, wherein said copper complex comprises the reaction product of copper carbonate and a chelating agent in an aqueous environment.

10. The composition of claim 7, wherein said copper complex is made by combining from about 3 to about 50% by weight of the complete composition of water, from about 5 to about 60% by weight of the complete composition of a chelating agent, and from about 2 to about 22% by weight of the complete composition of copper carbonate.

11. A composition comprising water treated with an algaecidally effective amount of the composition of claim 1.

12. A composition comprising less than about 5% by weight of a terpene, from about 1 to about 20% by weight of an emulsifier comprising the reaction product of tall oil fatty acid and an alcohol amine, and from about 10 to about 99% by weight of a copper complex, wherein said terpene is present in an amount effective to function as a wetting agent.

13. A composition comprising from about 0.1 to less than about 5% by weight of a terpene, from about 1 to about 20% by weight of an emulsifier comprising the reaction product of tall oil fatty acid and an alcohol amine, from about 3 to about 50% by weight of water, from about 5 to about 60% by weight of a chelating agent, and from about 2 to about 22% by weight copper carbonate.

14. A composition comprising from about 0.1 to less than about 5% by weight of a terpene, from about 0.5 to about 11% by weight of a tall oil fatty acid, from about 0.4 to about 10% by weight of an alcohol amine, from about 3 to about 50% by weight of water, from about 5 to about 60% by weight of a chelating agent, and from about 2 to about 22% by weight copper carbonate.

15. A composition comprising from about 0.1 to less than about 5% by weight of a terpene, from about 0.5 to about 11% by weight of a tall oil fatty acid, from about 5 to about 70% by weight of an alcohol amine, from about 3 to about 50% by weight of water, and from about 2 to about 22% by weight copper carbonate.

16. A method of controlling algae in water, comprising the step of adding to water an algaecidally effective amount of the composition of claim 1.

17. A method of controlling algae in a body of water, comprising the step of spraying onto the surface of a body of water an algaecidally effective amount of the composition of claim 1.

18. The composition of claim 1, wherein said terpene is present as from about 0.1 to about 1% by weight of the composition.

19. The composition of claim 12, comprising less than about 1% by weight of said terpene, wherein said terpene is present in an amount effective to function as a wetting agent.

* * * * *